US012690769B2

(12) United States Patent
Takahashi

(10) Patent No.: US 12,690,769 B2
(45) Date of Patent: Jul. 28, 2026

(54) FUNDUS INFORMATION ACQUISITION METHOD AND FUNDUS INFORMATION ACQUISITION DEVICE

(71) Applicant: DEEPEYEVISION INC., Tochigi (JP)

(72) Inventor: Hidenori Takahashi, Tochigi (JP)

(73) Assignee: DEEPEYEVISION INC., Tochigi (JP)

( * ) Notice: Subject to any disclaimer, the term of this patent is extended or adjusted under 35 U.S.C. 154(b) by 184 days.

(21) Appl. No.: 18/565,988

(22) PCT Filed: Oct. 20, 2022

(86) PCT No.: PCT/JP2022/039052
§ 371 (c)(1),
(2) Date: Nov. 30, 2023

(87) PCT Pub. No.: WO2023/074517
PCT Pub. Date: May 4, 2023

(65) Prior Publication Data
US 2024/0260830 A1 Aug. 8, 2024

(30) Foreign Application Priority Data
Oct. 29, 2021 (JP) ................................. 2021-178241

(51) Int. Cl.
*A61B 3/14* (2006.01)
*A61B 3/12* (2006.01)
(52) U.S. Cl.
CPC . *A61B 3/14* (2013.01); *A61B 3/12* (2013.01)

(58) Field of Classification Search
CPC ........... A61B 3/0025; A61B 3/10; A61B 3/12; A61B 3/14
See application file for complete search history.

(56) References Cited

U.S. PATENT DOCUMENTS

2014/0085604 A1 3/2014 Michaels et al.
2021/0059522 A1 3/2021 Shimizu et al.

FOREIGN PATENT DOCUMENTS

WO 2019/146792 A 8/2019

OTHER PUBLICATIONS

Patent Cooperation Treaty, International Search Report, Application No. PCT/JP2022/039052, dated Dec. 27, 2022, in 6 pages.

*Primary Examiner* — Jack Dinh
(74) *Attorney, Agent, or Firm* — PROCOPIO, CORY, HARGREAVES & SAVITCH LLP

(57) ABSTRACT

To provide a fundus information acquisition method that allows observation and photography to be conducted using an optical system of a simple and easy configuration without the need for accurate alignment of the imaging unit with a test eye even when there is a distance from the test eye. A fundus information acquisition method is provided with an infinity-corrected optical system that uses an imaging unit placed opposite an objective lens that causes light passing through the objective lens to form an image as part of a fundus image of a test eye, where at least a site defined by a range of a pupil of the test eye out of a cornea and a crystalline lens of the same test eye is used as the objective lens opposed to a fundus of the test eye.

13 Claims, 6 Drawing Sheets

FUNDUS INFORMATION ACQUISITION METHOD AND FUNDUS INFORMATION ACQUISITION DEVICE

CROSS-REFERENCE TO RELATED APPLICATIONS

This application is US National Stage of International Patent Application PCT/JP2022/039052, filed Oct. 20, 2022, which claims benefit of priority from Japanese Patent Application 2021-178241, filed Oct. 29, 2021, the contents of both of which are incorporated herein by reference.

TECHNICAL FIELD

The present disclosure relates to a fundus information acquisition method and a fundus information acquisition device.

BACKGROUND ART

In fundus observation, an eyeball includes a cornea and a crystalline lens, which are convex lenses with high refractive indices. Therefore, light from the fundus is strongly refracted by the cornea and the crystalline lens and images are formed at a very close distance from the eyeball, and thus even if an examiner conduct observation by looking into the eye of a subject, the examiner cannot observe the fundus of a test eye directly. Therefore, in fundus observation, an observation method of either a direct ophthalmoscopic optical system or an indirect ophthalmoscopic optical system is used.

In the direct ophthalmoscopic optical system, the fundus is observed by canceling out the refraction of the cornea and crystalline lens with a concave lens and thereby bringing the fundus into focus. In so doing, the examiner needs to bring the examiner's own eye close to the test eye, and consequently can observe an area of only about 10 degrees in front of the pupil in the eyeball.

In the indirect ophthalmoscopic optical system, by using a convex lens, the examiner generates an intermediate image of an inverted image of the fundus and thereby observes the fundus of the test eye. The examiner can observe an area of about 50 degrees in front of the pupil in the eyeball. In so doing, if projected light is aligned with a visual axis of the test eye, the fundus cannot be seen due to corneal reflex. On the other hand, if projected light is tilted several degrees from the visual axis of the test eye, that part of the fundus which is to be observed does not match that part of the fundus which is illuminated by the projected light, and thus the fundus cannot be observed. Therefore, it is common practice for the examiner to observe the fundus of the test eye while avoiding corneal reflex by slightly tilting the projected light by one to two degrees from the visual axis of the test eye or by using a ring-shaped light or the like.

For fundus photography, a so-called stand-mounted fundus camera is generally used. The fundus camera is a type of indirect ophthalmoscopic optical system and is an advanced version of a conventional indirect ophthalmoscopic optical system. A scanning laser ophthalmoscope (SLO) is also a type of system resulting from further advancing an indirect ophthalmoscopic optical system. The SLO, which uses laser for fundus observation, becomes highly reflective if a strong convex lens is used, and thus the SLO has been developed by making complicated improvements, such as the use of concave mirrors instead of some convex mirrors, to an observation method that uses a conventional indirect ophthalmoscope.

In recent years, in developed countries in particular, retinal diseases such as age-related macular degeneration and diabetic retinopathy leading to loss of eyesight have been increasing with aging and increases in diabetes. As a method for early detection of such diseases in a simple and easy way, production and sales of so-called mobile fundus cameras have been attracting attention. Such mobile fundus cameras are strongly required even in developing countries where ownership rates of typical fundus cameras are low.

Based on the above situation, in recent years, mobile fundus cameras that can be used in combination with a smart phone and the like have been produced and sold. For example, by specifying, as a problem to be solved, the provision of an device that allows both the anterior ocular segment and the fundus to be photographed easily when attached to a mobile terminal such as a smart phone, Patent Literature 1 describes, as a solution to the problem, the use of a close-up photographic device detachably attached to a mobile terminal equipped with a light source, a photographic camera lens, and a predetermined member.

CITATION LIST

Patent Literature

Patent Literature 1: International Publication No. WO 2019/146792

SUMMARY OF INVENTION

However, such a mobile fundus camera needs to photograph at a distance very close to the test eye. In particular, with a fundus camera that uses an LED lamp of a smart phone or the like, because the fundus of the test eye is observed and photographed while being illuminated by the light from the LED lamp, there is a problem in that the pupil of the test eye contracts (undergoes miosis) greatly due to dazzle, making it difficult for the examiner to conduct observation.

Therefore, for example, an observation method that uses a mydriatic agent is being considered, but with this observation method, it is very dangerous if examination of the anterior ocular segment is insufficient and a narrow-angle eye is overlooked (the narrow-angle eye is a condition in which the distance between the cornea and the crystalline lens of the test eye becomes short, and when the pupil is dilated and the iris moving to the periphery comes into contact with the cornea and blocks the exit for the liquid in the eye, a sudden increase in pressure will occur in the eye, which may result in loss of eyesight). Thus, the use of the mydriatic agent in developing countries in particular, involves high risk. Besides, the examiner needs to project viewing light onto the pupil of the test eye within tolerances of 1 mm in all x, y, z position coordinates, posing a problem in that accurate alignment is difficult.

In addition, an objective lens of about 20 D (D is the reciprocal of focal length(m)) needs to be placed at a distance of a few centimeters from the eyeball, posing a problem in that it is difficult to photograph at a distance of 10 cm or above. Regarding a method for placing the objective lens at a distance of a few centimeters from the eyeball, parts for use to fix a light-emitting unit and an imaging unit at appropriate distances from the test eye are produced around the world, but it remains unchanged that the smart phone and the like need to be aligned accurately with the test eye. Furthermore, it is totally impossible to photograph naturally in daily life by making sure that the test eye will not notice that the fundus is being photographed.

The present disclosure has been made in view of the above problems and has an object to provide a fundus information acquisition method that allows observation and photography to be conducted using an optical system of a simple and easy configuration without the need for accurate alignment of an imaging unit with a test eye even when there is a sufficient distance from the test eye.

To solve the above problems, the present inventors have conducted active studies. As a result, the present inventors have found that the problems can be solved by a fundus information acquisition method provided with an infinity-corrected optical system, and thereby completed the present invention.

Namely, a fundus information acquisition method according to one aspect of the present disclosure is provided with an infinity-corrected optical system that uses an imaging unit placed opposite an objective lens that causes light passing through the objective lens to form an image as part of a fundus image of a test eye, where at least a site defined by a range of a pupil of the test eye out of a cornea and a crystalline lens of the test eye is used as the objective lens opposed to a fundus of the test eye, the method comprising a fundus image acquisition step of acquiring an image of the test eye including the fundus image reflected in the range of the pupil of the test eye in the imaging unit.

A fundus information acquisition method according to another aspect of the present disclosure is provided with an infinity-corrected optical system that uses an imaging unit placed opposite an objective lens that causes light passing through the objective lens to form an image as part of a fundus image of a test eye, where at least a site defined by a range of a pupil of the test eye out of a cornea and a crystalline lens of the same test eye is used as the objective lens opposed to a fundus of the test eye, the method comprising: a successive fundus image acquisition step of acquiring a plurality of test eye images including the fundus image reflected in the range of the pupil of the test eye while changing relative position of the test eye and the imaging unit; a position information identification step of identifying a position of the fundus image in the fundus based on information obtained from the fundus image; and a fundus image composition step of generating a composite fundus image of the test eye by arranging the plurality of fundus images based on the position in the fundus identified on the fundus image.

In the fundus information acquisition method, the position information identification step may identify the position of the fundus image in the fundus based on characterizing portions appearing on the fundus image by originating from components of the test eye.

In the fundus information acquisition method, the characterizing portions appearing on the fundus image are a first reflex from a portion including a corneal vertex of the test eye and a second reflex from an anterior lens capsule of the test eye, and the position information identification step may identify the position of the fundus image in the fundus based on a positional relationship between a bright spot of the first reflex and a bright spot of the second reflex.

In the fundus information acquisition method, when a plurality of fundus images acquired in the successive fundus image acquisition step do not cover all regions on the fundus of the test eye, the fundus image composition step may identify an eye position corresponding to a region in which a fundus image is not acquired by the successive fundus image acquisition step using a mathematical model trained by machine learning or deep learning, and the successive fundus image acquisition step may be carried out at the eyeball position thereby to acquire a fundus image in the region in which a fundus image is not acquired by the successive fundus image acquisition step.

In the fundus information acquisition method, when a plurality of fundus images acquired in the successive fundus image acquisition step do not cover all regions on the fundus of the test eye, the fundus image composition step may supplement a fundus image in the region in which a fundus image is not acquired by the successive fundus image acquisition step with a standard image of an entire fundus of the test eye using a mathematical model trained by machine learning or deep learning.

In the fundus information acquisition method, the plurality of fundus images acquired in the successive fundus image acquisition step may be used as training data for the mathematical model.

In the fundus information acquisition method, the fundus image composition step may make a focus correction to each of the plurality of fundus images acquired in the successive fundus image acquisition step and/or the composite fundus image of the test eye using one or more super-resolution techniques.

The fundus information acquisition method may further comprise an abnormal-site estimation information acquisition step of acquiring information for estimation of presence or absence of an abnormal site and information for estimation of a position of an abnormal site by inputting the composite fundus image to a mathematical model trained by machine learning or deep learning using image data on retinal diseases as learning data.

The fundus information acquisition method may further comprise a display step of displaying the composite fundus image on a display unit of the imaging unit.

In the fundus information acquisition method, the imaging unit may be a camera of a mobile terminal.

In the fundus information acquisition method, the imaging unit may be a camera of a stationary device.

In a fundus information acquisition device according to one aspect of the present disclosure, based on an infinity-corrected optical system that uses an imaging unit placed opposite an objective lens that causes light passing through the objective lens to form an image as part of a fundus image of a test eye, where at least a site defined by a range of a pupil of the test eye out of a cornea and a crystalline lens of the test eye is used as the objective lens opposed to a fundus of the test eye, the imaging unit acquires an image of the test eye including the fundus image reflected in the range of the pupil of the test eye.

Advantageous Effects of Invention

The present disclosure allows observation and photography to be conducted using an optical system of a simple and easy configuration without the need for accurate alignment of the imaging unit with a test eye even when there is a sufficient distance from the test eye.

DESCRIPTION OF EMBODIMENTS

Now, the present disclosure will be outlined with reference to the accompanying drawings. Note that the embodiments described below are intended to facilitate the understanding of the present disclosure, but are not to be interpreted as limiting the present disclosure. Also, various changes can be made to the present disclosure without departing from the gist of the present disclosure. Furthermore, those skilled in the art can adopt embodiments obtained by replacing elements described below with equivalents and such embodiments are also included in the scope of the present disclosure.

1. Fundus Information Acquisition Device 4

Figure 1:
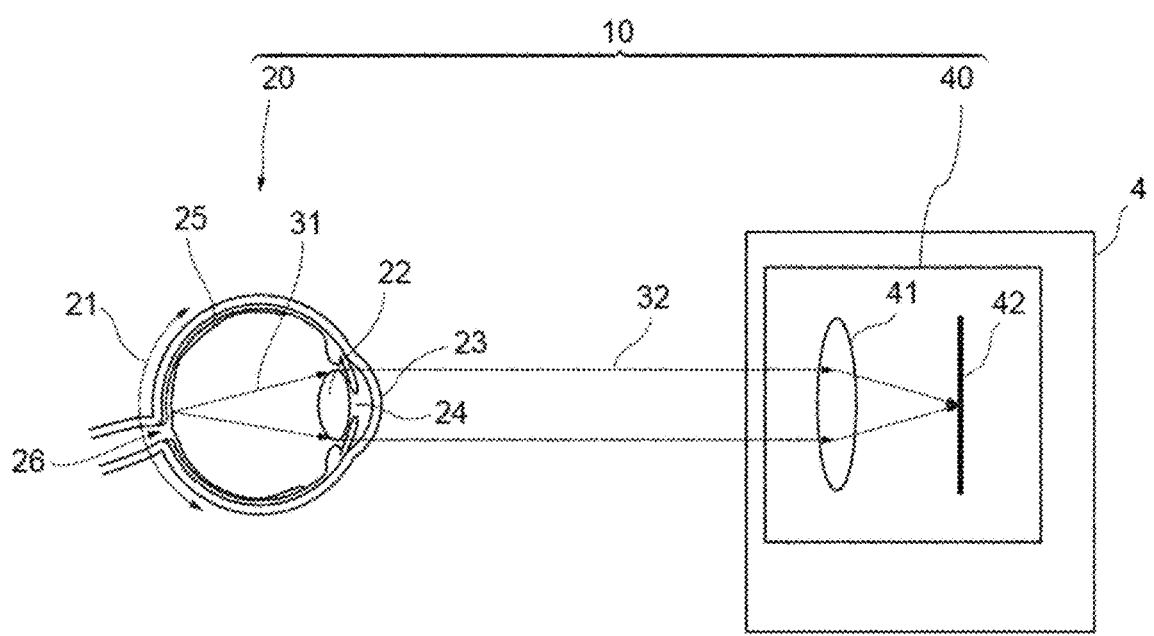
FIG. 1 is a schematic diagram of an infinity-corrected optical system.

FIG. 1 is a diagram showing an example of a fundus information acquisition device 4 configured to acquire images of a test eye based on an infinity-corrected optical system 10. The fundus information acquisition device 4 according to the present embodiment acquires an image of a test eye 20 including a fundus image reflected in a range of the pupil of the test eye 20 in an imaging unit 40 based on an infinity-corrected optical system 10 that uses the imaging unit 40 placed opposite an objective lens that causes reflected light 31 passing through the objective lens to form an image as part of the fundus image of the test eye 20, where at least a site defined by the range of the pupil 24 of the test eye 20 out of the cornea 23 and the crystalline lens 22 of the same test eye is used as the objective lens opposed to the fundus 21 of the test eye 20.

<Hardware Configuration>

Figure 9:
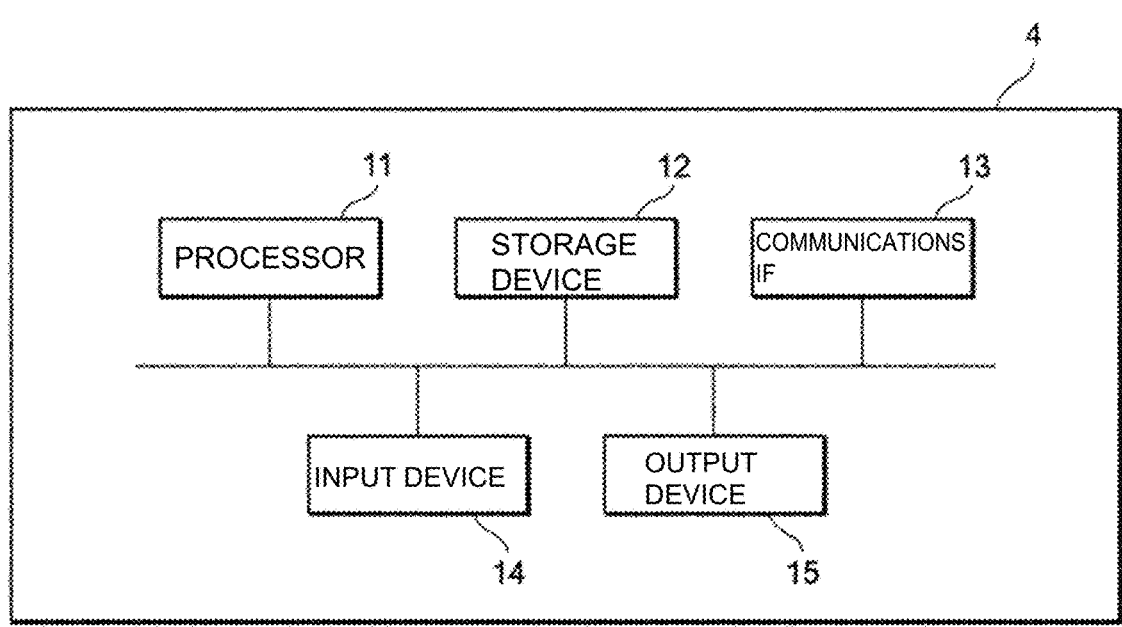
FIG. 9 is a hardware configuration of a fundus information acquisition device according to one embodiment.

FIG. 9 is a diagram showing an exemplary hardware configuration of the fundus information acquisition device 4. The fundus information acquisition device 4 includes processors 11 such as a CPU (central processing unit) and a GPU (graphical processing unit); storage devices 12 such as a memory, an HDD (hard disk drive), and/or SSD (solid state drive); a communications IF (interface) 13 used to conduct wired or wireless communications; input devices 14 configured to accept input operations; and output devices 15 configured to output information. The input devices 14 include a keyboard, a touch panel, a mouse, and/or a microphone. The output devices 15 include a display, a touch panel, and/or a speaker.

In the present embodiment, the imaging unit 40 may be configured to be included in the input devices 14. Alternatively, the imaging unit 40 may be configured to be included in an external device of the fundus information acquisition device 10 such that fundus images will be inputted from any of the input devices 14 by being acquired by the imaging unit 40 via a communications line or the like.

<Functional Block Configuration>

Figure 10:
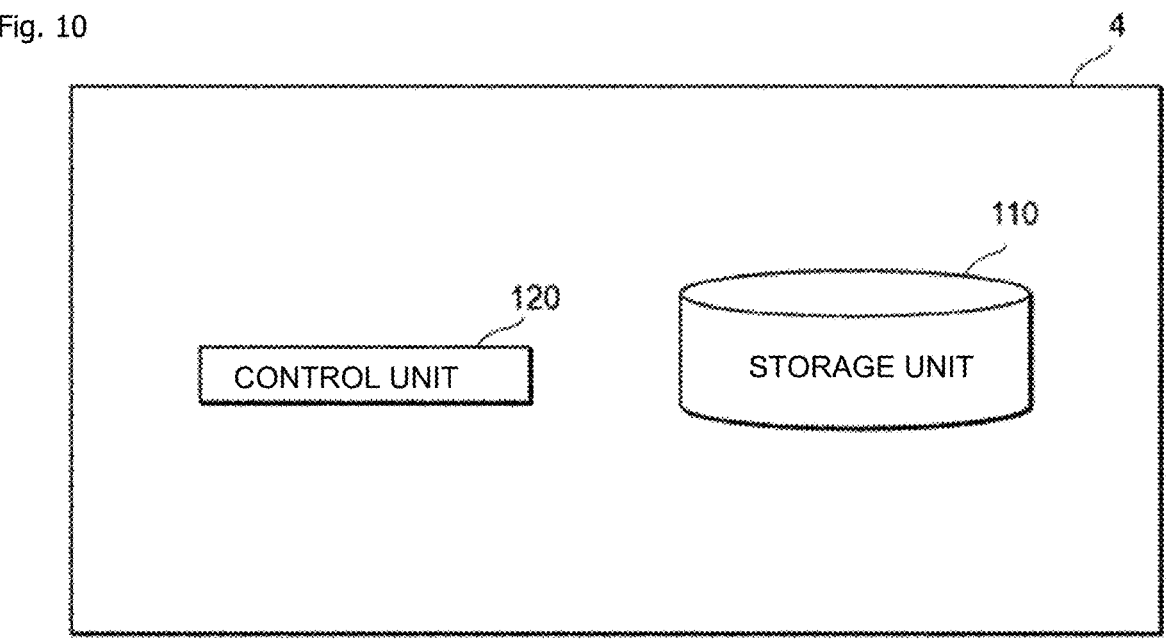
FIG. 10 is a functional block configuration of a fundus information acquisition device according to one embodiment.

FIG. 10 is a diagram showing an exemplary functional block configuration of a fundus information acquisition device 4. The fundus information acquisition device 4 includes a storage unit 110 and a control unit 120. The storage unit 110 can be implemented using the storage devices 12 of the fundus information acquisition device 4. On the other hand, the control unit 120 can be implemented when a processor 11 of the fundus information acquisition device 4 executes a program stored in a storage device 12. The program can also be stored in a storage medium. The storage medium storing the program may be a non-transitory computer readable medium. The non-transitory storage medium is not particularly limited, but may be a storage medium such as a USB memory or a CD-ROM.

Figure 8:
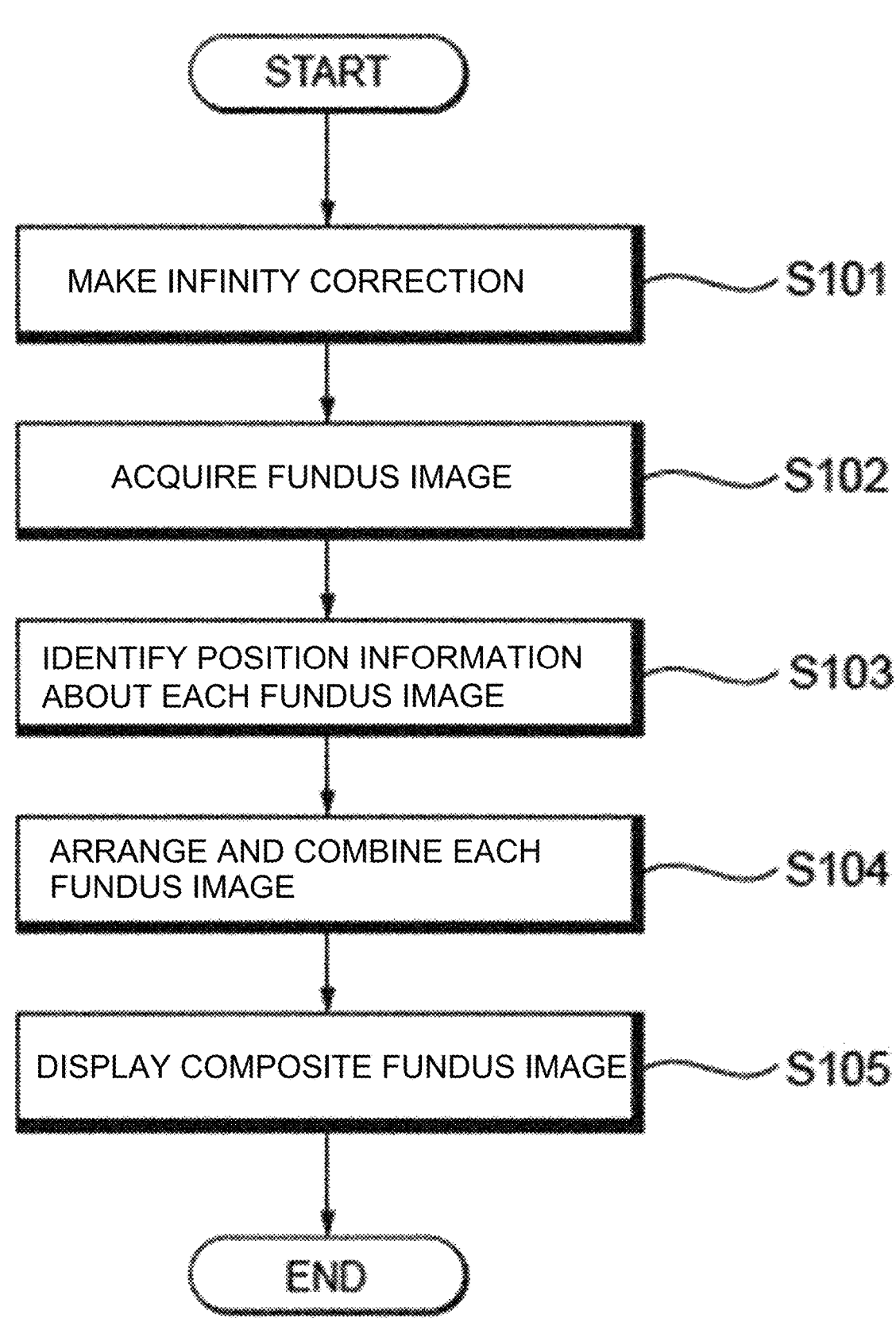
FIG. 8 is a flowchart of an operation performed by a fundus information acquisition device according to one embodiment.

FIG. 8 is a flowchart of steps related to an operation performed by the fundus information acquisition device 4 according to one embodiment of the present disclosure. The steps are carried out by the control unit 120 of the fundus information acquisition device 4. Each of the steps will be described in detail below using FIG. 8.

The fundus information acquisition device 4 includes an infinity-correction step S101 and a fundus image acquisition step S102 and acquires fundus information about the test eye 20 by carrying out these steps. The fundus information acquisition device 4 may also include a position information identification step S103, a fundus image composition step S104, and a display step S105. Furthermore, the fundus information acquisition device 4 may include other steps as required.

1.1. Infinity-Correction Step S101

As shown in FIG. 8, the infinity-correction step S101 is designed to construct the infinity-corrected optical system 10. Here, the infinity-corrected optical system is configured such that light passing through an objective lens will form a parallel light flux. According to the present embodiment, as shown in FIG. 1, in the infinity-corrected optical system 10, the reflected light 31 from the fundus 21 of the test eye 20 to be observed does not form an image on the crystalline lens 22 and the cornea 23, which are objective lenses, but enters an imaging lens 41 of the imaging unit 40 as a parallel light flux 32 at infinity and forms an image on an imaging device 42 via the imaging lens 41. Using the imaging unit 40, the fundus information acquisition device 4 acquires an image of the test eye 20 including the fundus image reflected in the range of the pupil of the test eye.

Accurate alignment of the imaging unit with the test eye is necessary for fundus observation and fundus photography that are based on an indirect ophthalmoscopic optical system used as a conventional technique. In addition to requiring accurate alignment of the imaging unit with the test eye fundus photography based on direct ophthalmoscopic optical system similarly used as a conventional technique needs to photograph at a very close distance from the test eye, and consequently illumination with light and the like at a close distance may involve risks.

On the other hand, according to the present embodiment, by constructing the infinity-corrected optical system 10, because there is no need to adjust positions of the imaging lens and the like to position of an intermediate image formed through the objective lens unlike the conventional indirect ophthalmoscopic optical system, distances of the objective lens, imaging lens, and the like can be adjusted freely, making it possible to conduct fundus observation and the like in a simple and easy way. Besides, because the imaging unit 40 can be kept at a sufficiently long distance from the test eye 20, the imaging unit 40 can be used safely in a simple and easy way.

According to the present embodiment, the means of urging the subject to look into infinity is not specifically limited, but an aspect in which the fundus information acquisition device 4 is provided with fixation target projection means can be taken as an example. Consequently, the fundus information acquisition device 4 includes a fixation lamp configured to emit visible light and can present a fixation target to the subject by lighting the fixation lamp and direct the test eye to look in the direction of infinity.

Here, regarding the infinity according to the present embodiment, it is not essential for the light from the fundus 21 to become a parallel light flux in the strict sense after passing through the crystalline lens 22 and the cornea 23. When the subject looks into infinity strictly, needless to say it is preferable that the light leaving the fundus 21 and passing through the crystalline lens 22 and the cornea 23 should make up a parallel light flux, it is sufficient if the light flux approximates a parallel light flux to the extent that the test eye 20 can be observed with a certain accuracy that satisfies minimum practical requirements. The certain accuracy that satisfies minimum practical requirements is sufficient if at least information about the color of the fundus 21 of the test eye 20 is available.

If fundus information obtained in the present embodiment includes at least information about the color of the fundus 21, the fundus information can be used for diagnosis of glaucoma or optic atrophy. If information about the shape of the fundus 21 is included, the fundus information can be used for diagnosis of retinal diseases and the like as well.

The imaging unit 40 of the fundus information acquisition device 4 that acquires an image of the test eye 20 based on an infinity-corrected optical system 10 may use, as required, two or more imaging lenses that make up the imaging lens 41 as a system. When two or more imaging lenses are used, the lens that focuses onto the imaging device 42 is referred to as a first imaging lens and the other lens is referred to as a second imaging lens. The second imaging lens may form an intermediate image.

1.1.1. Objective Lens

In the present embodiment, at least a site 51 defined by a range of the pupil 24 of the test eye 20 out of the cornea 23 and the crystalline lens 22 of the test eye 20 is used as the objective lens opposed to the fundus 21 of the test eye 20. It is sufficient if the objective lens is configured such that the reflected light 31 from the fundus 21 will become a parallel light flux 32 when the subject looks into infinity, and if the subject is using eye glasses or the like, the objective lens means an optical system made up integrally of at least a site defined by a range of the pupil 24 of the test eye 20 out of the cornea 23 and the crystalline lens 22 of the test eye 20 and the eye glasses.

1.1.1.1. Pupil 24

The pupil is an aperture surrounded by the iris of the eye and changes its diameter according to light quantity. Changes in the pupil diameter contributes to adjustment of the light quantity projected onto the retina. Therefore, when the test eye 20 is exposed to intense light, the pupil 24 contracts and the pupil diameter is reduced, and consequently the extent to which the fundus 21 can be observed tends to become reduced. Therefore, according to the present embodiment, preferably fundus images are acquired with ambient light minimized.

1.1.1.2. Crystalline Lens 22

The crystalline lens is a transparent convex lens-shaped body existing in front part of the eyeball and causes images to be formed on the retina by refracting light from outside. The crystalline lens 22 is adjusted automatically, becoming thick for close vision and becoming thin for distant vision and thereby allows images of objects from various distances to be brought into focus.

According to the present embodiment, by urging the subject to look into infinity, the thickness of the crystalline lens 22 is adjusted such that the crystalline lens 22 will be focused on infinity.

1.1.1.3. Cornea 23

The cornea is a transparent film covering the anterior portion of the eyeball, and plays a convex lens-like role in conjunction with the crystalline lens.

1.1.2. Imaging Unit 40

According to the present embodiment, the imaging unit 40 includes the imaging lens 41 and imaging device 42 for use to focus a parallel light flux 32 passing through the crystalline lens 22 and the cornea 23, which are objective lenses. It is sufficient that the imaging lens 41 has a desired refractive index.

The imaging device 42 has sensitivity to at least visible light and infrared light. The imaging device 42 is not specifically limited, but preferably has, for example, a binning function of processing some adjacent photoelectric conversion elements as a single pixel. Consequently, even in the case of reflected light 31 from the fundus 21 of the test eye 20 with small quantity of light, the imaging device 42 exhibits sensitivity high enough not to get in the way of obtaining fundus images.

Figure 6:
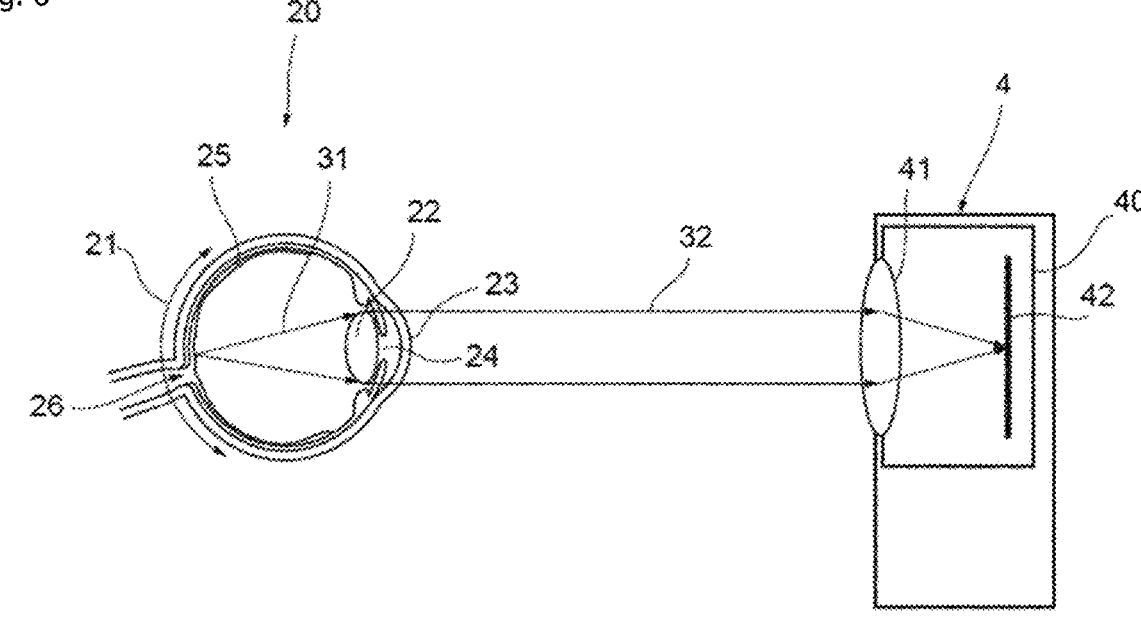
FIG. 6 is a schematic diagram showing an example in which a mobile terminal is used as a fundus information acquisition device 4.

FIG. 6 is a schematic diagram showing an example in which a mobile terminal is used as a fundus information acquisition device 4. For example, a camera of the mobile terminal is used as the imaging unit 40. The mobile terminal is not specifically limited, but an information processing device such as a smart phone, a tablet computer, a notebook PC, or a workstation can be taken as an example. Using the camera of a mobile terminal as the imaging unit 40, a simple and easy optical system based on the mobile terminal can be constructed as shown in FIG. 6, making it possible to acquire fundus information in a simple and easy way. Here, a terminal means a piece of equipment capable of performing a key role in conducting communications with other equipment by being connected to a circuit or a network.

Figure 7:
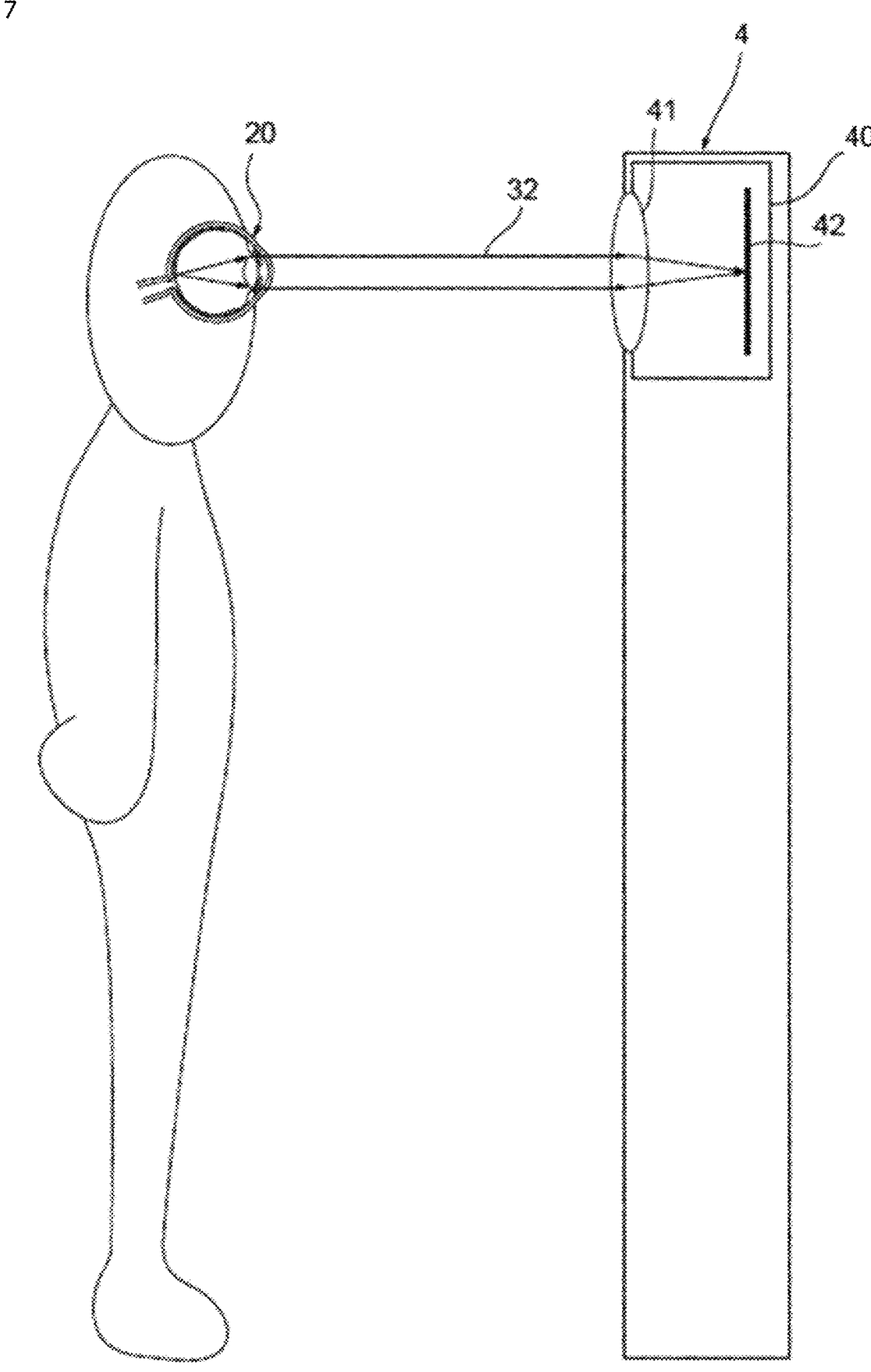
FIG. 7 is a schematic diagram showing an example in which a stationary device is used as the fundus information acquisition device 4.

FIG. 7 is a schematic diagram showing an example in which a stationary device is used as the fundus information acquisition device 4. For example, a camera of the stationary device is used as the imaging unit 40. If a stationary device is used as the fundus information acquisition device, as shown in FIG. 7, when the subject moves by being opposed to the stationary device, the relative position of the test eye 20 and the imaging unit 40 can be changed in a simple and easy way. Besides, the fundus image acquisition step S102 according to the present embodiment can be carried out successively without making the subject perform any operation for a certain period of time.

When a stationary device is used as the imaging unit 40, distance between the test eye 20 and the imaging unit 40 tends to become larger than when a mobile terminal is used as the imaging unit 40, and resolution of the fundus image obtained tends to decrease accordingly. Therefore, preferably, fundus information is acquired with an increased resolution using the second imaging lens configured to form an intermediate image of the fundus image of the test eye 20. Note that according to the present embodiment, the second imaging lens means a lens that forms an intermediate image, but does not mean a lens focused on the imaging device 42.

The stationary device may be a smart mirror. The use of the smart mirror allows the subject to photograph naturally in daily life without thought. Here, the smart mirror is a mirror terminal equipped with a mirror capable of Internet connection and the like and capable of reflecting a figure of the subject himself/herself as well as with a camera capable of photographing the test eye.

The imaging unit 40 may include a first imaging lens, a lamp provided around the first imaging lens, and a polarizing plate provided in a preceding stage of the first imaging lens. By including a lamp, which is illuminating means, the imaging unit 40 can improve accuracy of fundus information based on return light from the test eye 20. The provision of the polarizing plate makes it possible to remove surface reflection of light from objects other than the test eye 20 and thereby make the color of the resulting fundus image, in particular, vivid.

The lamp provided around the first imaging lens may be a ring-shaped lamp placed on an outer circumference of the first imaging lens. The use of such a lamp allows light emitted to the test eye 20 from the lamp to illuminate the test eye 20 more uniformly, making it possible to obtain high-accuracy fundus images.

When a mobile terminal or a camera of a stationary device is used as the imaging unit 40, the lamp provided around the first imaging lens may be a built-in lamp of the mobile terminal or stationary device. This will make it possible to acquire fundus image information in a more simple and easy way.

1.2. Fundus Image Acquisition Step S102

As shown in FIG. 8, the fundus image acquisition step S102 is designed to acquire fundus images. As means of acquiring fundus images conventionally known means can be used. Image acquisition means is not specifically limited, and images can be acquired by photographing using photographic means such as a camera. Preferably, the image acquisition means includes illuminating means to acquire images of the test eye based on return light from the test eye. The illuminating means can improve accuracy of information especially about the color of the fundus.

According to one aspect, the fundus image acquisition step S102 includes a successive fundus image acquisition step. The successive fundus image acquisition step is designed to acquire a plurality of fundus images successively by changing the relative position of the test eye 20 and the imaging unit 40. Detailed description will be given below.

1.2.1. Means of Changing Relative Position of Test Eye 20 and Imaging Unit 40.

As means of changing the relative position of the test eye 20 and the imaging unit 40, a conventionally known method can be used. The method is not specifically limited, and, for example, the relative position may be changed by making the subject change the direction in which the subject looks into infinity, without changing the position of the imaging unit 40, or may be changed by changing the position of the imaging unit 40 rather than changing the position of the subject.

Means of making the subject change the direction in which the subject looks into infinity is not specifically limited, but the use of fixation target projection means for presenting a plurality of fixation targets can be taken as an example. The fixation target projection means includes a fixation lamp configured to emit visible light, presents a plurality of fixation targets to the subject by lighting up the fixation lamp, and thereby directs the test eye 20 to look in a plurality of directions.

The images are used in the fundus image composition step S104, and the number of images to be acquired is not specifically limited, but preferably, for example, 30 or more images are acquired, more preferably 100 or more images are acquired, and still more preferably 300 or more images are acquired.

1.3. Position Information Identification Step S103

As shown in FIG. 8, the position information identification step S103 is designed to identify the position of the fundus image in the fundus 21 based on information obtained from a test eye image. Preferably, the step is carried out so as to identify the position of the fundus image in the fundus 21 based on characterizing portions appearing on the test eye image by originating from components of the test eye 20. This will make it possible to improve the accuracy of the fundus information that can be acquired.

Figure 2:
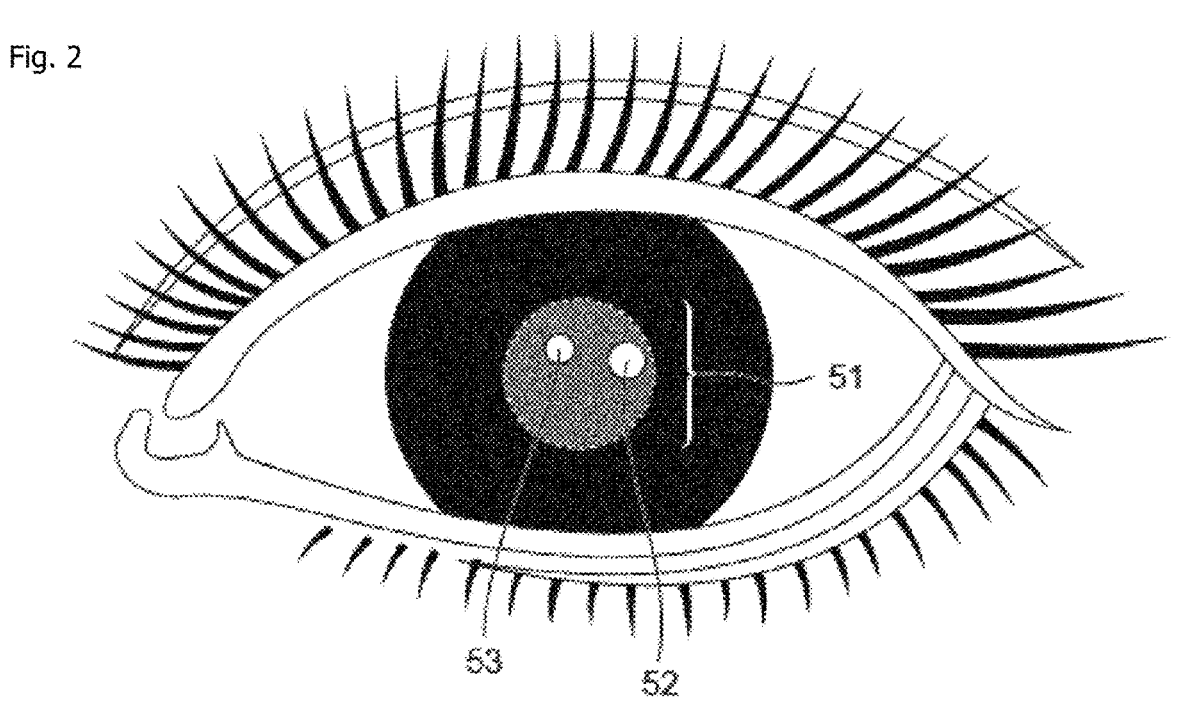
FIG. 2 is a diagram showing an example of a test eye image including a fundus image acquired in a fundus image acquisition step.
Figure 4:
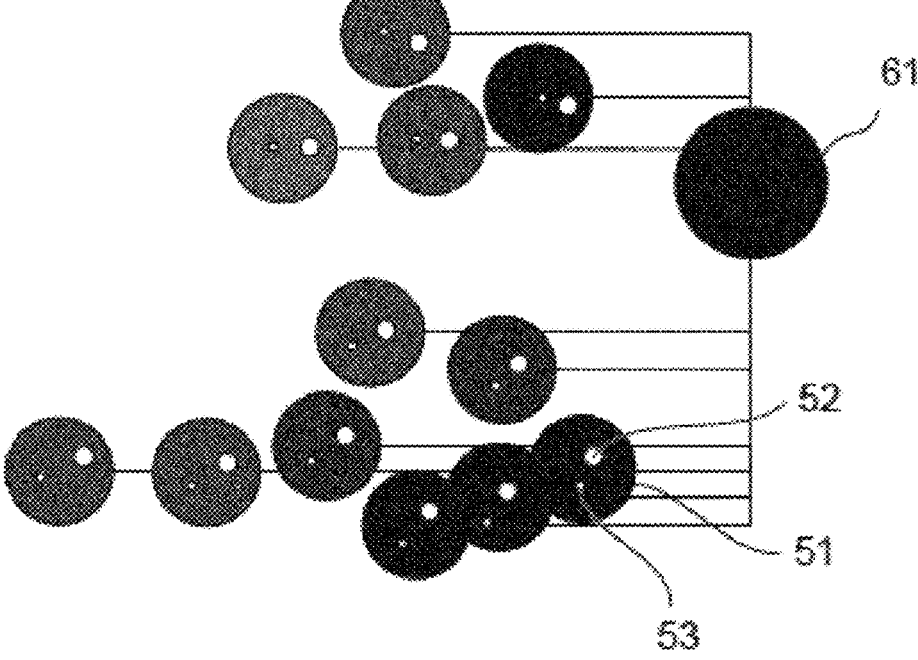
FIG. 4 is an exemplary diagram in which a plurality of fundus images are arranged.

FIG. 2 is a diagram showing an example of a test eye image including a fundus image acquired by fundus image acquisition means. FIG. 4 is an exemplary diagram in which a plurality of fundus images are arranged. In one embodiment of the position information identification step, assuming that characterizing portions are a first reflex from a portion including a corneal vertex of the test eye 20 and a second reflex from an anterior lens capsule of the test eye 20, the position of the fundus image in the fundus 21 is identified based on a positional relationship between a bright spot 52 of the first reflex and a bright spot 53 of the second reflex. Specifically, based on distance between 52 and 53, distance between a center point 61 of the test eye 20 and the fundus image are identified, and moreover, by placing the fundus image such that a straight line passing through 52 and 53 will pass through an eyeball center point 61 orientation of the fundus image from the center point 61 of the test eye 20 is identified. This identification method can reduce the number of computational processes performed by a computer in composite fundus image generation, making it possible to acquire fundus information quickly in a simple and easy way.

Figure 3:
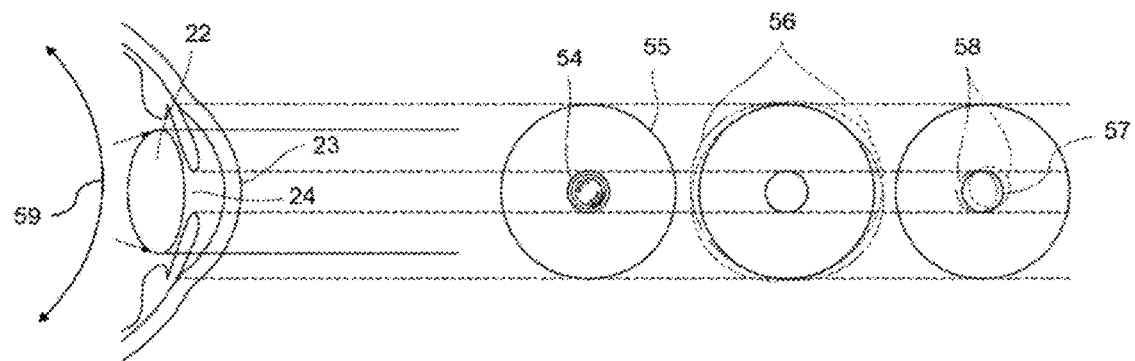
FIG. 3 is an exemplary diagram showing changes in a scene reflected in a test eye, changes in a corneal limbus of the test eye, movements of the pupil center in the corneal limbus, or changes in a pupil border, according to one embodiment.

FIG. 3 is an exemplary diagram showing changes in a scene reflected in the test eye such as movements of a scene reflected in the pupil of the test eye, changes in the corneal limbus of the test eye, movements of the pupil center in the corneal limbus, or changes in the pupil border. In particular, in the infinity-corrected optical system 10 in which incident light is insufficient such as when only ambient light is used, a possible embodiment of the position information identification step includes a method of identifying the distance between the center point 61 of the test eye 20 and the fundus image by detecting changes in a scene 54 reflected in the test eye 20, caused by rotational movements 59 of the eyeball of the test eye 20, a method of identifying the distance between the center point 61 of the test eye 20 and the fundus image by detecting changes 56 in the corneal limbus caused by rotational movements 59 of the eyeball such as a change in the corneal limbus 55 from a circular shape to a substantially elliptical shape occurring in response to rotational movements 59 of the eyeball, a method of identifying the distance between the center point 61 of the test eye 20 and the fundus image by detecting movements 58 of the pupil center in the corneal limbus caused by rotational movements 59 of the eyeball, or a method of identifying the distance between the center point 61 of the test eye 20 and the fundus image by detecting changes in the pupil border 57 caused by rotational movements 59 of the eyeball. More preferably, these identification methods are used in combination.

Regarding other embodiments of the position information identification step, conventionally known means can be used to identify the position of a fundus image in the fundus 21, and although not specifically limited, an embodiment that includes feature point detection means for detecting a feature point of an image, and means for simultaneously storing a feature value and coordinate data of the detected feature point can be taken as an example. Here, because fundus images are acquired form the same test eye 20, some of a plurality of fundus images contain a common fundus region and a common feature point, and consequently based on one fundus image, position information of other fundus images can be identified. More specifically, for example, position information can be identified by extracting vascular intersections and the like shown in each fundus image as feature points, finding out common intersection pairs through correlation matching of image data around the vascular intersections between two fundus images, and superimposing the two fundus images with reference to the positions of the retrieved intersection pairs.

Here, the sentence that "some of a plurality of fundus images contain a common fundus region and a common feature point," means not that a common fundus region and a common feature point are photographed on all the fundus images of the same test eye 20, but that among a plurality of fundus images acquired, there are images that contain a common fundus region and a common feature point although the common fundus region is not necessarily an identical fundus region.

1.4. Fundus Image Composition Step S104

As shown in FIG. 8, the fundus image composition step S104 arranges a plurality of fundus images based on the positions identified by the position information identification step S103, and generates a composite fundus image of the test eye 20.

According to the present embodiment, since the infinity-corrected optical system 10 is used, the range of the fundus 21 shown in the fundus image becomes smaller than in the indirect ophthalmoscopic optical system, but the fundus image composition step S104 makes it possible to generate a composite fundus image for use to observe the fundus 21 in a wider range.

Furthermore, the fundus image composition step S104 eliminates the need for accurate alignment of the imaging unit 40 with the test eye 20, and makes it possible to conduct high-definition observation and photography even if there is a considerable distance between the imaging unit 40 and the test eye 20.

Figure 5:
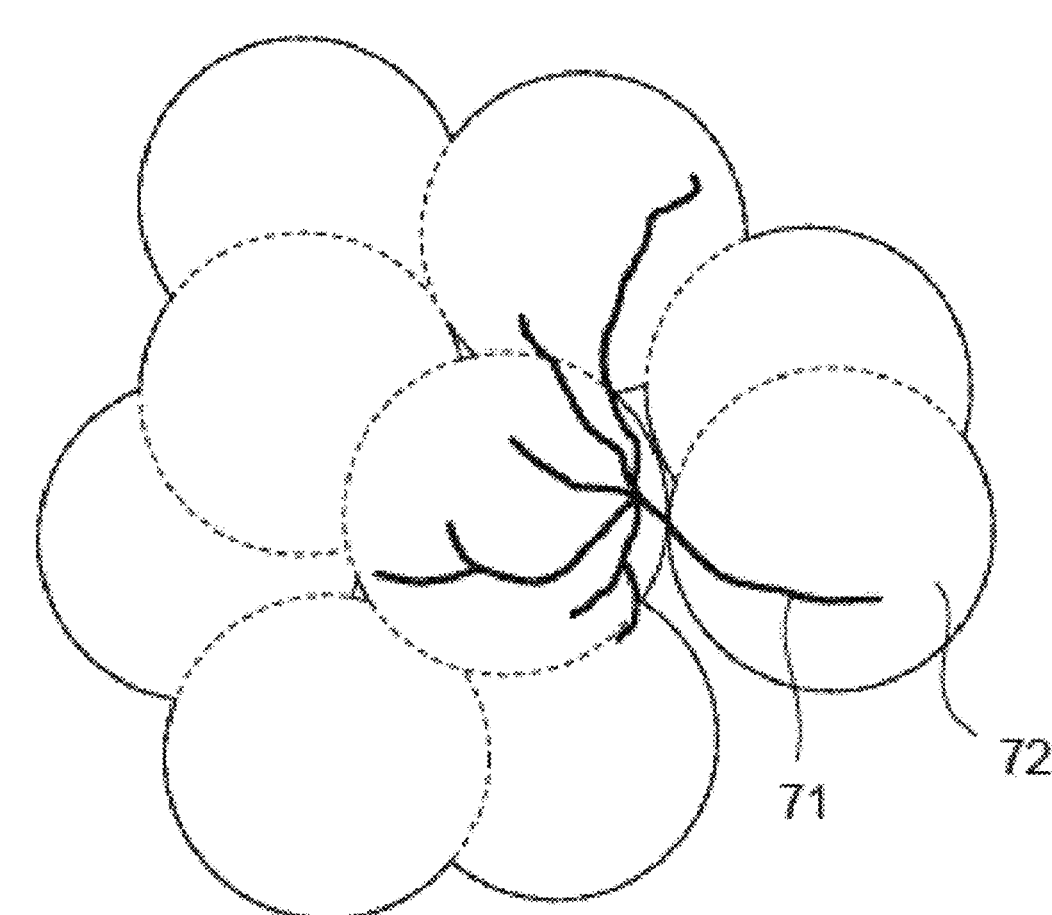
FIG. 5 is a schematic diagram of a composite fundus image according to one embodiment.

FIG. 5 is an example of a composite fundus image. Although not specifically limited, a composite fundus image can be generated, for example, by arranging fundus images 72 based on the position information identified by the position information identification step S103, and then connecting the fundus images 72 by superimposing common fundus regions including blood vessels 71 and the like shown in each of the fundus images 72.

Here, when the plurality of fundus images 72 acquired in the fundus image acquisition step S102 do not cover all regions on the fundus 21 of the test eye 20, a first embodiment is used, whereby a fundus image 72 in the region in which a fundus image is not acquired by the fundus image acquisition step S102 can be supplemented by identifying an eyeball position at which the fundus image 72 corresponding to a region in which a fundus image 72 is not acquired by the fundus image acquisition step S102 can be captured and carrying out the fundus image acquisition step S102 at the identified eyeball position, where the eyeball position can be identified using a mathematical model trained by machine learning or deep learning.

The second embodiment can supplement the fundus image 72 in the region in which a fundus image is not acquired by the fundus image acquisition step S102 using a standard image of the entire fundus of the test eye 20 based on a mathematical model trained by machine learning or deep learning. The standard image is a fundus image or the like acquired by a conventionally known image acquisition method. The conventionally known standard image acquisition method is not specifically limited, and a fundus photography and the like using a wide-angle scanning ophthalmoscope can be taken as an example.

Here, as training data for the mathematical model in the first and second embodiments, the plurality of fundus images 72 acquired in the fundus image acquisition step S102 can be used.

Furthermore, in the third embodiment, as a method for supplementing the fundus image 72 in the region in which a fundus image is not acquired by the fundus image acquisition step S102, if the plurality of fundus images 72 acquired in the fundus image acquisition step S102 is used as training data for the mathematical model, the fundus image 72 in the region in which a fundus image is not acquired by the fundus image acquisition step S102 can be generated and supplemented. Consequently, although the number of computations performed by the computer increases, because there is no need to prepare the standard image of the fundus 21 of the subject, fundus observation can be conducted in a simple and easy way.

Here, a learning model trained by machine learning (hereinafter referred to as a machine learning model) is an example of a mathematical model. The machine learning model has a predetermined model structure and parameters that change with the learning process, and includes a model whose identification accuracy is improved when process parameters are optimized based on experience obtained from training data. That is, the machine learning model learns optimum process parameters through a learning process. Regarding algorithms for the machine learning model, for example, Support Vector Machine, Logistic Regression, Random Forest, and Neural Network are available for use. Preferably, a neural network is used from the viewpoint of acquiring a composite fundus image even when volume of training data is small, but the type of neural network is not specifically limited. Some of the machine learning model that undergo the learning have already undergone some learning using training data, and the others have not undergone any learning.

Preferably, the fundus image composition step S104 makes a focus correction to each of the plurality of fundus images 72 acquired in the fundus image acquisition step S102 and/or the composite fundus image of the test eye 20 using one or more super-resolution techniques. Consequently, the resolution of the fundus image can be improved. Note that the super-resolution technique converts an existing low-resolution (LR) image into a high-resolution (HR) image by an image processing method using a software algorithm and, to put it simply, improves resolution by pixel shift.

1.5. Display Step S105

As shown in FIG. 8, the display step S105 displays a composite fundus image. Preferably, the fundus information acquisition device 4 according to the present embodiment includes the display step S105. Consequently, fundus information about the subject can be checked in a simple and easy way.

When the display step S105 is provided, if the plurality of fundus images 72 acquired in the fundus image acquisition step S102 do not cover all regions on the fundus 21 of the test eye 20, a first embodiment is used, whereby the subject can be directed to look in a necessary direction in a simple and easy way in identifying an eyeball position at which the fundus image 72 corresponding to a region in which a fundus image 72 is not acquired by the fundus image acquisition step S102 can be captured and carrying out the fundus image acquisition step S102 at the identified eyeball position, where the eyeball position can be identified using a mathematical model trained by machine learning or deep learning.

1.6. Other Steps

The fundus information acquisition device 4 according to the present embodiment may include other steps as required in addition to the steps described above. Although not specifically limited, examples of other steps include an abnormal-site estimation information acquisition step. The present embodiment may further include an abnormal-site estimation information acquisition step of acquiring information for estimation of the presence or absence of an abnormal site and information about an estimated position of an abnormal site by inputting the composite fundus image to a mathematical model trained by machine learning or deep learning using image data on retinal diseases as learning data. This will be useful for early, simple, and easy detection of retinal diseases and the like.

INDUSTRIAL APPLICABILITY

Although not specifically limited, the present disclosure can acquire still images and moving images used for ophthalmologic examinations, for example, using a mobile terminal such as a smart phone. Compared to fundus observation methods that use a slit-lamp microscope or a handheld slit-lamp microscope, the fundus information acquisition method according to the present disclosure can be constructed very inexpensively without using special parts, and thus is expected to disseminate widely throughout the world.

The present disclosure can also be used clinically. Specifically, in examination by an ophthalmologist, a stand-mounted fundus camera is used for observation and diagnosis of the test eye, but examination of little children and bedridden elderly involves difficulty and requires skill. However, according to the present disclosure, regardless of the posture of the patient, by simply urging the subject to look into infinity, fundus images can be taken very easily using a mobile terminal or the like, and subsequently if generated by commonly used composite image acquisition means, a composite fundus image can be used for observation and diagnosis. Therefore, the present disclosure is expected to be used in telemedicine for remote areas and in assistance for developing countries.

Furthermore, the present disclosure can similarly be used for fundus observation and photography of animals. In particular, the present disclosure makes it possible to shoot still images and moving images of eyes of animals including pet animals as well as large zoo animals whose test eyes the imaging unit is especially difficult to align with, and thereby acquire ophthalmologic findings of the animals.

Furthermore, by making AI analyze the findings as Big Data, diagnostic accuracy of ophthalmologists can be improved. Eventually, the present disclosure will be used as self-diagnostic tools of subjects, allowing ophthalmology itself to advance further.

REFERENCE SIGNS LIST

4 . . . fundus information acquisition device, 10 . . . infinity-corrected optical system, 20 . . . test eye, 21 . . . fundus, 22 . . . crystalline lens, 23 . . . cornea, 24 . . . pupil 25 . . . retina, 26 . . . optic papilla, 31 . . . light, 32 . . . parallel light flux, 40 . . . imaging unit, 41 . . . imaging lens, 42 . . . imaging device, 51 . . . site defined by range of pupil, 52 . . . bright spot of first reflex, 53 . . . bright spot of second reflex, 54 . . . scene reflected in test eye, 55 . . . corneal limbus, 56 . . . changes in corneal limbus, 57 . . . pupil border, 58 . . . movements of pupil center in corneal limbus, 59 . . . rotational movements of eyeball, 61 . . . eyeball center point, 71 . . . blood vessels, 72 . . . fundus image, 11 . . . processor, 12 . . . storage device, 13 . . . communications IF, 14 . . . input device, 15 . . . output device, 110 . . . storage unit, 120 . . . control unit

The invention claimed is:

1. A fundus information acquisition method provided with an infinity-corrected optical system that uses an imaging unit placed opposite an objective lens that causes light passing through the objective lens to form an image as part of a fundus image of a test eye, where at least a site defined by a range of a pupil of the test eye out of a cornea and a crystalline lens of the same test eye is used as the objective lens opposed to a fundus of the test eye, the method comprising:

a successive fundus image acquisition step of acquiring a plurality of test eye images including the fundus image reflected in the range of the pupil of the test eye while changing relative position of the test eye and the imaging unit;

a position information identification step of identifying a position of the fundus image in the fundus based on information obtained from the test eye images; and a fundus image composition step of generating a composite fundus image of the test eye by arranging the plurality of fundus images based on the position in the fundus identified on the fundus image.

2. The fundus information acquisition method according to claim 1, wherein the position information identification step identifies the position of the fundus image in the fundus based on characterizing portions appearing on the test eye images by originating from components of the test eye.

3. The fundus information acquisition method according to claim 2, wherein the characterizing portions appearing on the test eye images are a first reflex from a portion including a corneal vertex of the test eye and a second reflex from an anterior lens capsule of the test eye, and the position information identification step identifies the position of the fundus image in the fundus based on a positional relationship between a bright spot of the first reflex and a bright spot of the second reflex.

4. The fundus information acquisition method according to claim 2, wherein the characterizing portions appearing on the test eye images is a scene reflected in the test eye, and the position information identification step identifies the position of the fundus image in the fundus based on changes in the scene reflected in the test eye.

5. The fundus information acquisition method according to claim 2, wherein

US 12,690,769 B2

15                                                   16 the characterizing portions appearing on the test eye images are corneal limbus of the test eye, a pupil center in the corneal limbus or a pupil border, and the position information identification step identifies the position of the fundus image in the fundus based on the corneal limbus of the test eye, movements of the pupil center in the corneal limbus, or changes in the pupil border.

6. The fundus information acquisition method according to claim 1, wherein when a plurality of fundus images acquired in the successive fundus image acquisition step do not cover all regions on the fundus of the test eye, the fundus image composition step identifies an eye position corresponding to a region in which a fundus image is not acquired by the successive fundus image acquisition step, using a mathematical model trained by machine learning or deep learning, and the successive fundus image acquisition step is carried out at the eyeball position thereby to supplement a fundus image in the region in which a fundus image is not acquired by the successive fundus image acquisition step.

7. The fundus information acquisition method according to claim 6, wherein the plurality of fundus images acquired in the successive fundus image acquisition step are used as training data for the mathematical model.

8. The fundus information acquisition method according to claim 1, wherein when a plurality of fundus images acquired in the successive fundus image acquisition step do not cover all regions on the fundus of the test eye, based on a mathematical model trained by machine learning or deep learning, the fundus image composition step supplements a fundus image in the region in which a fundus image is not acquired by the successive fundus image acquisition step using a standard image of the entire fundus of the test eye.

9. The fundus information acquisition method according to claim 1, wherein in the fundus image composition step, a focus correction is made to each of the plurality of fundus images acquired in the successive fundus image acquisition step and/or to the composite fundus image of the test eye using one or more super-resolution techniques.

10. The fundus information acquisition method according to claim 1, further comprising an abnormal-site estimation information acquisition step of acquiring information for estimation of presence or absence of an abnormal site and information for estimation of a position of an abnormal site by inputting the composite fundus image to a mathematical model trained by machine learning or deep learning using image data on retinal diseases as learning data.

11. The fundus information acquisition method according to claim 1, further comprising a display step of displaying the composite fundus image.

12. The fundus information acquisition method according to claim 1, wherein the imaging unit is a camera of a mobile terminal.

13. The fundus information acquisition method according to claim 1, wherein the imaging unit is a camera of a stationary device.

* * * * *